United States Patent [19]

Yarger

[11] Patent Number: 5,697,911
[45] Date of Patent: Dec. 16, 1997

[54] PLUG FOR A WOUND DRAIN

[76] Inventor: Richard J. Yarger, 4908 Douglas Dr., Yakima, Wash. 98908

[21] Appl. No.: 374,486
[22] Filed: Jan. 17, 1995
[51] Int. Cl.⁶ .................................................. A61M 5/170
[52] U.S. Cl. ........................... 604/158; 604/256; 604/167
[58] Field of Search ...................................... 604/158, 164, 604/167, 256, 236, 238; 606/191

[56] References Cited

U.S. PATENT DOCUMENTS

| | | | |
|---|---|---|---|
| 396,754 | 1/1889 | Mayfield | 604/256 X |
| 611,454 | 9/1898 | Longden | 604/256 X |
| 1,920,006 | 7/1933 | Dozier | 604/256 X |
| 3,467,088 | 9/1969 | Robinson | 604/158 X |
| 3,516,403 | 6/1970 | Cournet | 604/158 X |
| 3,589,368 | 6/1971 | Jackson et al. | 128/350 |
| 3,877,464 | 4/1975 | Vermes | 604/158 X |
| 4,359,053 | 11/1982 | Benjamin | 128/339 |
| 4,445,896 | 5/1984 | Gianturco | 604/238 |
| 4,714,461 | 12/1987 | Gabel | 604/256 X |
| 4,973,305 | 11/1990 | Goltzer | 604/158 X |
| 5,084,014 | 1/1992 | Picha et al. | 604/54 |
| 5,104,383 | 4/1992 | Shichman | 604/167 |
| 5,209,737 | 5/1993 | Ritchart et al. | 604/167 |
| 5,261,895 | 11/1993 | Kablik | 604/249 |
| 5,300,035 | 4/1994 | Clement | 604/167 |
| 5,312,362 | 5/1994 | Pfolsgraf et al. | 604/167 |
| 5,330,488 | 7/1994 | Goldrath | 604/158 X |
| 5,591,132 | 1/1997 | Carrie | 604/158 |

*Primary Examiner*—Sam Rimell
*Attorney, Agent, or Firm*—Christensen O'Connor Johnson & Kindness PLLC

[57] ABSTRACT

A plug (40) is used to plug the end of a drain tube (38). The drain tube is introduced into a patient during a medical procedure to drain the surgical site. The drain tube is introduced through an opening or incision in the patient leading to the interior of the patient's body. A medical instrument (36) is used to extract the drain tube out through the opening in the patient's body. The plug includes an elongated insertion section (42) of a cross-sectional size for slidable insertion into the end of the drain tube. The plug also includes a grasping section (48) projecting longitudinally from the insertion section and conveniently graspable by the medical instrument. The grasping section includes a tip portion (56) opposite the insertion section, and a base portion (54) located between the tip and the insertion section. The cross-sectional size of the base portion is greater than the cross-sectional size of the tip portion, wherein the cross-sectional size of the grasping section decreases in a direction extending away from the insertion section.

21 Claims, 2 Drawing Sheets

PLUG FOR A WOUND DRAIN

FIELD OF THE INVENTION

The present invention relates generally to medical equipment, and more particularly to medical equipment used for inserting objects into the body of a patient during a surgical procedure.

BACKGROUND OF THE INVENTION

Typically, surgical procedures require the insertion of a drain tube to drain the surgical site while the patient is recovering from surgery. In use, the distal end of the drain tube is located at the surgical site in the patient's body, and the proximal end extends out of the patient's body, with the skin of the patient sutured snugly around the tube to retain it in place. While the patient is recovering, the proximal end of the tube is connected to a suction/collection device to drain fluids that would otherwise accumulate at the surgical site.

Frequently, the drain tube is extended out of the body through an incision separate from the major incision through which the surgical procedure is performed. There are two principal reasons for this. First, it is omen desired to position the tube so that fluids accumulating at the surgical site are drained downward by gravity. Many times this requires a separate, smaller incision to properly position the drain tube. Second, it may be medically inadvisable to extend a drain tube through a major incision while the patient is recovering. In general, it is difficult to suture large incisions around a drain tube so that the skin tissue is sealed around the tube to prevent fluid leakage. Hence, a separate, smaller incision is made to receive the drain tube.

When a separate, smaller incision is made to receive a drain tube, the tube is usually first inserted into the patient through the major surgical incision. Subsequently, a medical instrument is inserted through the smaller incision to grasp the proximal end of the drain tube. The medical instrument is then withdrawn to thread the drain tube through the smaller incision. The tube is withdrawn from the smaller incision until the distal end of the tube is properly positioned at the surgical site. Thereafter, the skin of the patient is sutured around the drain tube to retain it in place.

There are drawbacks with the foregoing procedure for threading a drain tube through a separate, smaller incision. First, often it is difficult to grasp the end of the drain tube with the medical instrument. Second, it is medically advisable to make the second, smaller incision as small as possible to minimize trauma to the patient, to minimize recovery time, and to facilitate sealing the tissue around the tube. However, the incision must be made large enough to accommodate the medical instrument while it is grasping the drain tube. More particularly, the medical instrument includes a pair of jaws that are used to grasp the tube. Generally, the incision must be made significantly larger than the cross-sectional area of the drain tube to accommodate the width of the jaws while they are in an expanded position, grasping the drain tube therebetween.

Problems also arise in laparoscopic medical procedures when inserting a drain tube into a patient. In a laparoscopic medical procedure, the surgery is accomplished through access ports. That is, small incisions are made in the patient, and an access port is inserted in each incision, giving medical personnel access to the interior of the body. Medical personnel then insert cameras and instruments through the access ports to perform the medical procedure.

When a laparoscopic procedure occurs within the intra-abdominal cavity of a patient, it is common to pressurize the cavity with a gas to enable the camera to provide medical personnel with a better view of the body's interior and to provide more room to perform the medical procedure. Usually, the access ports are constructed with valves which may be closed when the patient's intra-abdominal cavity is pressurized so that the gas cannot escape, and thus, deflate this space. In addition, the access ports normally have internal seals that seal against laparoscopic medical equipment that extends through the ports. Hence, pressurization gas is substantially prevented from escaping from the intra-abdominal cavity during the insertion and use of laparoscopic medical equipment through the access ports.

In a laparoscopic medical procedure, a drain tube is placed in position by threading the proximal end of the drain tube through a first access port. Thereafter, a medical instrument is inserted through a second access port to grasp the proximal end of the drain tube. The medical instrument is then withdrawn from the second access port while grasping the drain tube to draw the distal end of the tube into the intra-abdominal cavity through the first access port. The medical instrument is withdrawn until the distal end of the tube is properly positioned at the surgical site. Alternatively, the entire drain tube is threaded into the intra-abdominal cavity and the distal end of the tube positioned at the desired location before the proximal end of the tube is withdrawn through a second access port site with a medical instrument. Once the drain tube has been properly positioned, the second access port is removed and the skin of the patient is sutured snugly around the drain tube to retain the tube.

Problems exist with inserting a drain tube into a patient during a laparoscopic procedure. First, while the drain tube is being threaded through the laparoscopic operating port, the pressurization gas escapes from the abdominal cavity through the drain tube itself. Second, when a medical instrument is used to grasp the drain tube, many times the jaws of the surgical instrument are expanded to a width, with the drain tube therebetween, such that the surgical instrument cannot be withdrawn through the laparoscopic operating port. As such, the operating port must be removed to withdraw the proximal end of the drain tube, thereby losing inflation pressure.

The present invention addresses the foregoing problems with inserting a drain tube into a patient.

SUMMARY OF THE INVENTION

The present invention provides a plug for the end of a drain tube introduced into a patient during a medical procedure. The drain tube is introduced through an opening, or incision in the patient's body leading to the interior of the patient's body. A medical instrument is used to extract the drain tube out through the opening in the patient's body.

The plug includes an elongated insertion section of a cross-sectional area sized for slidable insertion into the end of the drain tube. A grasping section, for grasping by the medical instrument, projects longitudinally from the insertion section. The grasping section includes a tip portion opposite the insertion section and a base portion located between the tip portion and the insertion section. The cross-sectional size of the base portion is greater than the cross-sectional size of the tip portion, wherein the cross-sectional size of the grasping section decreases in the direction extending away from the insertion section.

The grasping section includes a thin-section member projecting longitudinally from the tip for presenting a thin cross-section for grasping by the medical instrument. In a preferred embodiment, the thin-section member is in the form of a tab. Preferably the tab includes a generally planar area bounded by a rim forming a raised lip to facilitate grasping and retention by the medical instrument. In an alternate embodiment, the thin-section member is in the form of a loop.

In a preferred embodiment a retaining section is located between the insertion section and the grasping section. The retaining section has a cross-sectional size less than the cross sectional size of the base portion of the grasping section. The plug is inserted into the drain tube until the end of the drain tube extends past the insertion section, and over the retaining section. The tube tends to contract around the smaller cross-sectional area of the retaining section to retain the plug in engagement within the drain tube.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

Figure 1:
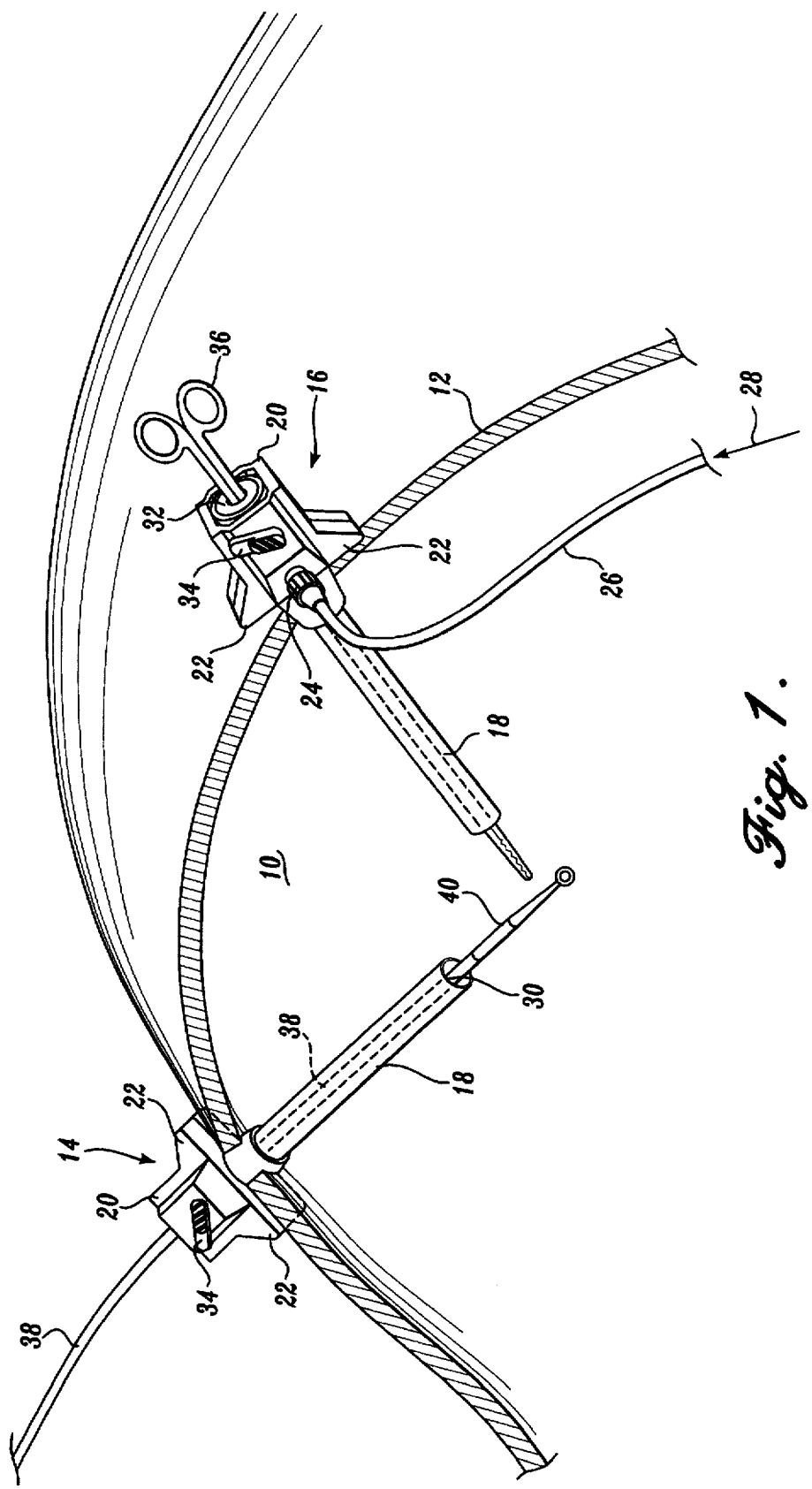
FIG. 1 illustrates a plug constructed in accordance with the present invention, being used to introduce a drain tube into the body of a patient.

Referring to FIG. 1, a representation of a patient's intra-abdominal cavity 10 is illustrated. This is the area within a patient's abdomen, behind the abdominal wall 12, where internal organs are located. Two conventional, laparoscopic operating ports 14 and 16 are shown in FIG. 1, having been inserted through the abdominal wall 12 of the patient, such that the ports extend into the intra-abdominal cavity 10. Before proceeding with a detailed description of the present invention, a brief description of the laparoscopic operating ports 14 and 16 is first provided.

Laparoscopic operating ports 14 and 16 both include a cylindrically-shaped, hollow tube 18 extending forwardly from an enlarged, generally rectangular body portion 20. At the forward end of the body portion 20, adjacent the hollow tube 18, are two shoulders 22, projecting laterally from opposite sides of the body portion 20. Each shoulder is generally in the shape of a right triangle to present an abutment for the user's fingers when grasping the port. The hollow tube 18 mates with the body portion 20 so that the longitudinal axes of each part are coincident. The laparoscopic operating ports 14 and 16 are inserted into the intra-abdominal cavity 10 up to near the body portion 20. The remaining portions of the laparoscopic operating ports 14 and 16 are disposed outside the body of the patient.

Laparoscopic operating port 16 includes a valve 24, for the introduction of pressurization gas into the intra-abdominal cavity 10. Valve 24 on laparoscopic operating port 16 is shown attached to a delivery tube 26. The other end of the tube 26, in turn, connects to a source of pressurization gas 28. When valve 24 on laparoscopic operating port 16 is open, pressurization gas flows from source 28, through tube 26, through valve 24, and through the laparoscopic operating port 16 into the intra-abdominal cavity 10 of the patient. The intra-abdominal cavity 10 is normally pressurized in this way with carbon dioxide during a laparoscopic surgery to approximately 15 mm Hg. This properly inflates the intra-abdominal cavity 10, permitting medical procedures to be more easily accomplished within the intra-abdominal cavity.

The body portions 20 of the laparoscopic operating ports 14 and 16 have an internal passageway 30 extending through it coincident with the longitudinal axis of the body portion. The hollow tube 18 mates with the body portion 20 of the laparoscopic operating port 14, 16, such that internal passageway 30 extends from hollow tube 18 through body portion 20 of the laparoscopic operating port.

The laparoscopic operating ports 14, 16 include an internal gate valve, not shown, for closing off the internal passageway 30 within the body portions 20. Pivot handles 34 are provided for manually operating the valves. When the valve is closed, its handle 34 is positioned generally perpendicularly to the longitudinal axis of hollow tube 18 and body portion 20. Ideally, the valve is spring biased in closed position. When the handle 34 is rotated clockwise approximately 30°, the valve is opened.

A lip seal 32 is located just inside the rearward entrance to the internal passageway 30, in the body portion 20 of laparoscopic operating ports 14, 16. Seal 32 is generally annularly shaped and surrounds the internal passageway 30. Seal 32 is designed to extend around instruments that are inserted into laparoscopic operating ports 14, 16 through the gate valve as long as the exterior size of the instrument closely corresponds with the interior size of the port, to prevent fluid leakage through passageway 30 of the laparoscopic operating ports 14, 16, and into the environment.

A medical instrument 36 is shown inserted through laparoscopic operating port 16 and into the intra-abdominal cavity 10 of the patient. The seal 32, within the internal passageway of the port, presses against the circumference of the instrument 36 as it is inserted into the port and substantially prevents pressurization gas from escaping through the port while instrument 36 is being used.

A drain tube 38 is shown inserted through the laparoscopic operating port 14. The seal 32 within the laparoscopic operating port 14 presses against the tube 38 to prevent the leakage of fluid between the port and the tube.

Figure 2:
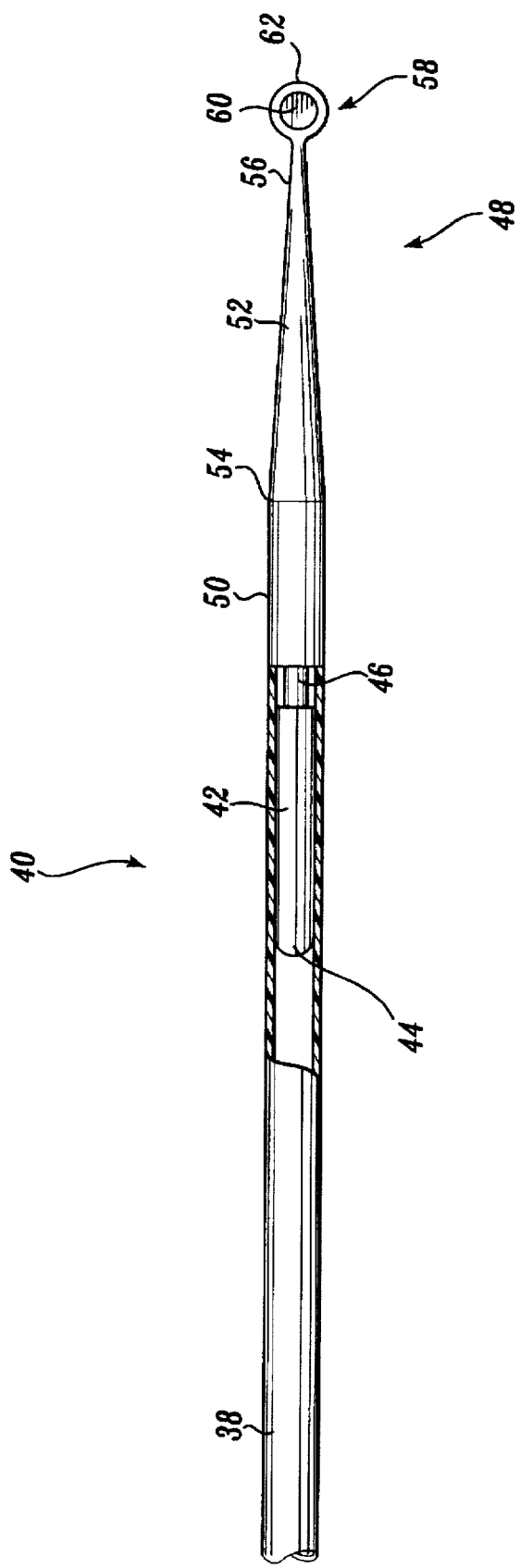
FIG. 2 is an enlarged view of the plug of FIG. 1, shown exploded away from the end of the drain tube.

A plug 40 in accordance with the present invention is shown inserted into the end of the drain tube 38 that extends through laparoscopic operating portion 14 into the intra-abdominal cavity 10 of the patient. Illustrated in FIG. 2 is an enlarged view of the plug 40, shown engaged with the drain tube 38. The plug 40 is preferably made of plastic, or other appropriate material, that is lightweight, substantially impervious to the passage of fluids, and has good moisture resistant properties to body fluids. In a preferred embodiment, the plug is of integral, one-piece construction. In alternate embodiments, the different sections of the plug may be separately formed and then combined.

The plug 40 includes an elongated insertion section 42 which is sized to be inserted into the end of the drain tube 38. Drain tubes, such as tube 38, used in laparoscopic surgery typically have internal diameters ranging from about 5 to 10 mm. The insertion section 42 is substantially cylindrical in shape having a rounded, generally hemispherical distal end 44. The hemispherical shape of the distal end 44 facilitates insertion of the plug 40 into the drain tube 38. Preferably, the diameter of the insertion section 42 is sized such that the insertion section 42 can be snugly slid into the end of the drain tube 38.

The plug 40 includes a retaining section 46 that extends longitudinally from the opposite end of the insertion section 42. The retaining section 46 is substantially cylindrical and is generally coaxially aligned with the insertion section 42. The retaining section is substantially shorter in length relative to the insertion section 42.

The diameter of the retaining section 46 is somewhat less, at least 0.02 inch, than the diameter of the insertion section 42. The insertion section 42 of the plug 40 is inserted into the drain tube 38 until the drain tube 38 extends beyond the proximal end of the insertion section, and surrounds the retaining section 46. Because the insertion section 42 snugly fits within the drain tube 38, the drain tube 38 is somewhat radially stretched as the insertion section is inserted therein. Thus, when the end of the drain tube 38 is slid past the proximal end of the insertion section 42, the drain tube tends to radially contract around the smaller diameter retaining section 46. This helps to retain the drain tube 38 over the insertion section 42 of the plug 40.

The plug also includes a gasping section 48 that extends longitudinally from the end of the retaining section 46, in the direction opposite the insertion section 42. The gasping section 48 preferably includes a generally cylindrical portion 50 that extends substantially coaxially from the retaining section 46. Ideally, but not mandatorily, the cylindrical portion is larger in diameter than the diameter of the insertion section 42. Thus, the plug 40 is inserted into the drain tube 38 until the end of the drain tube abuts the cylindrical portion 50. The larger diameter of the cylindrical portion 50 therefore serves as a stop to limit the distance the plug 40 is inserted into the drain tube 38. However, preferably the diameter of the cylindrical portion 50 does not exceed the outside diameter of the drain tube 38 as will be discussed more fully below.

The gasping section of the plug 40 also includes a generally conical portion 52 extending substantially coaxially from the end of the cylindrical portion 50, opposite the retaining section 46. The conical portion 52 gradually decreases in diameter to a distal tip 56.

A thin tab 58 extends from the tip 56. Preferably, the tab 58 is generally in the shape of a circle. However, in alternate embodiments of the present invention, the tab 58 may have other geometries, such as an oval, or a triangle by way of illustrative, nonlimiting examples. In the preferred embodiment, the tab 58 extends from the conical portion 52 such that the central axis of the tab 58 is generally aligned with the central axis of the conical portion 52.

Preferably, the tab 58 includes a generally planar central region 60 which is surrounded by a marginal rim 62 that projects on either side of the planar region 60 to form a raised, annular lip. The tab may be quite thin, but still be of sufficient structural integrity to be gasped by the instrument 36 and the attached tube 38 pulled through port 14 and out port 16, as described below. In this regard, if the plug 40 is composed of polypropylene, polyurethane or similar polymer plastic, the tab may be of a thickness of from about 0.01 to 0.04 inches. The lip may extend above and below the tab from about 0.01 to 0.04 inches.

In alternate embodiments, the planar area 60 of the tab can be eliminated, leaving a loop, or opening bounded by the rim 62. In the alternate embodiments, the rim 62 may be flexible. Thus the ring may be formed of string, nylon filament, plastic or other similar materials. In general, the purpose of the loop or tab 58 is to form a projecting member that presents a thin cross section for grasping by the medical instrument 36.

The plug 40 is used as follows: Prior to inserting the tube 38 through a laparoscopic operating port 14, the plug 40 is inserted into the drain tube 38. Thereafter, the plug 40 is inserted through the laparoscopic operating port 14 into the intra-abdominal cavity 10 of the patient, with the drain tube 38 trailing the plug 40. The plug 40 serves to substantially seal the end of the drain tube 38 so that pressurization gas within the intra-abdominal cavity 10 cannot escape through the drain tube while it is being inserted through the laparoscopic operating port 14.

After the plug 40 has been inserted into the intra-abdominal cavity 10, a medical instrument 36 is extended through a second laparoscopic operating port 16. The end of the instrument 36 is used to grasp the tab 58 at the end of the plug 40. Subsequently, the instrument 36 is withdrawn through the second laparoscopic operating port 16, thereby threading the plug 40 and drain tube 38 through the second laparoscopic operating port. Thus, it is desirable that the largest outside diameter of the plug 40 not exceed the outside diameter of the drain tube 38 to facilitate threading the plug and drain tube through the ports 14 and 16.

The drain tube 38 and plug 40 are withdrawn through the second laparoscopic operating port 16, until the trailing end of the drain tube 38 is properly positioned within the intra-abdominal cavity 10. When the trailing end of the drain tube 38 has been properly positioned and the surgical procedure completed, the laparoscopic operating ports 14 and 16 are removed. In particular, the second laparoscopic operating port 16 is withdrawn over the drain tube 38, and the skin tissue of the patient is sutured around the drain tube 38.

The use of the plug 40 in accordance with the present invention provides several advantages. First, the plug 40 serves to substantially seal the end of the drain tube 38 when it is being inserted through the laparoscopic operating port 14. This prevents pressurization gas in the intra-abdominal cavity 10 of the patient from escaping through the drain tube 38.

Second, the tab 58 at the end of the plug 40 facilitates grasping by the medical instrument 36. Moreover, tab 58 is thin enough that when the medical instrument 36 is grasping the plug 40, the jaws of the instrument do not remain open to the extent that the medical instrument cannot be withdrawn through the laparoscopic operating port 16. If the plug is not used so that the instrument must clamp on to the end of the tube 38 itself, the jaws of the medical instrument 36 remain open to the extent that the medical instrument cannot be withdrawn through the laparoscopic operating port 16.

Third, the rim 62 around the outer periphery of the tab 58 serves to facilitate a firm grasp by the medical instrument 36, i.e., help prevent the jaws of the instrument from disengaging from the tab. As noted above, in alternate embodiments, the central planar area 60 of the tab 58 may be removed, leaving a loop. Thus, in the alternate embodiments, a medical instrument having a hook-type end could be used to hook the loop.

Fourth, the conical portion 52 of the plug 40 serves to center the plug as it is being drawn into the second laparoscopic operating port 16 by the medical instrument 36. In alternate embodiments, the cylindrical portion 50 of the plug 40 can be eliminated.

The plug 40 also provides advantages in surgical procedures that are accomplished without the use of laparoscopic operating ports. As discussed above in the Background of the Invention section of this specification, a drain tube is typically extended out of a second, smaller incision, separate from the major incision through which the surgical procedure is performed. When it is desired to extend a drain tube 38 out of the second, smaller incision, the drain tube, having the plug 40 engaged therewith, may be inserted into the patient through the major incision. A medical instrument 36 inserted through the second, smaller incision, can be used to grasp tab 58 of the plug 40. The drain tube 38 is threaded through the second, smaller incision by withdrawing the medical instrument from the smaller incision.

Use of the plug 40 in the foregoing manner is advantageous because the medical instrument 36 can be used to more readily and securely grasp the tab 58 of the plug, as opposed to the drain tube 38 itself. Further, the tab 58 is significantly thinner than the drain tube 38. Thus, the jaws of the medical instrument 36 are substantially contracted even when grasping the tab 58. The medical instrument 36 can therefore be used to thread the drain tube 38 through a smaller incision to help reduce patient trauma and recovery time. The same advantages are provided in alternative embodiments where the planar area 60 of the tab is removed to form a loop for grasping by the medical instrument 36.

Finally, the conical portion 52 of the plug 40 serves to center the plug as it is being withdrawn through the second, smaller incision.

While a preferred embodiment of the invention has been illustrated and described, it will be appreciated that various changes can be made therein without departing from the spirit and scope of the invention.

The embodiments of the invention in which an exclusive property or privilege is claimed are defined as follows:

1. A plug for the end of a drain tube, the drain tube being for introduction into a patient during a medical procedure through an opening in the patient's body leading into the interior of the patient's body, wherein a medical instrument is used to extract the drain tube out through the opening in the patient's body, the plug comprising:
    (a) an elongated insertion section of a predetermined cross-sectional area for slidable insertion into one end of the drain tube;
    (b) a grasping section for grasping by the medical instrument, the grasping section projecting longitudinally from the insertion section, the grasping section including a tip portion opposite the insertion section and a base portion located between the tip portion and the insertion section, the base portion having a cross-sectional area larger than the cross-sectional area of the insertion section, wherein the cross-sectional area of the grasping section decreases in the direction extending away from the insertion section; and
    (c) a retaining section connecting the insertion section to the grasping section, the retaining section having a cross-sectional area smaller than the cross-sectional area of the base portion of the grasping section.

2. The plug of claim 1, wherein the grasping section includes a thin-section projection means projecting from the tip for presenting a thin cross-section for grasping by the medical instrument.

3. The plug of claim 2, wherein the thin-section projection means comprises a loop.

4. The plug of claim 2, wherein the thin-section projection means comprises a tab.

5. A plug for the end of a drain tube, the drain tube being for introduction into a patient during a medical procedure through an opening in the patient's body leading into the interior of the patient's body, wherein a medical instrument is used to extract the drain tube out through the opening in the patient's body, the plug comprising:
    (a) an elongated insertion section of a predetermined cross-sectional area for slidable insertion into one end of the drain tube; and
    (b) a grasping section for grasping by the medical instrument, the grasping section projecting longitudinally from the insertion section, the grasping section including a tip portion opposite the insertion section and a base portion located between the tip portion and the insertion section, the base portion having a cross-sectional area larger than the cross-sectional area of the insertion section, wherein the cross-sectional area of the grasping section decreases in the direction extending away from the insertion section, wherein the grasping section comprises:
        (i) a thin-section projection means projecting from the tip for presenting a thin cross section for grasping by the medical instrument, wherein the thin-section projection means comprises a tab having a generally planar area and a rim, the rim bounding the planar area to form a raised lip to facilitate grasping of the tab by the medical instrument.

6. The plug of claim 1, wherein the insertion section includes a first end portion connected to the grasping section, and a second portion projecting end being rounded in shape to facilitate inserting the second end into the end of the drain tube.

7. The plug of claim 1, wherein the base portion of the grasping section is substantially circular in shape, and the cross-sectional area of the grasping section gradually decreases along a path of travel from the base portion to the tip portion to form a generally conical shape.

8. A plug for the end of a drain tube, the drain tube being for introduction into a patient during a medical procedure through an opening in the patient's body leading into the interior of the patient's body, wherein a medical instrument is used to extract the drain tube out through the opening in the patient's body, the plug comprising:
    (a) an elongated insertion section of a predetermined cross-sectional area for slidable insertion into one end of the drain tube; and
    (b) a grasping section for grasping by the medical instrument, the grasping section projecting longitudinally from the insertion section, the grasping section including a tip portion opposite the insertion section and a base portion located between the tip portion and the insertion section, the base portion having a cross-sectional area larger than the cross-sectional area of the insertion section, wherein the cross-sectional area of the grasping section decreases in the direction extending away from the insertion section, wherein the base portion of the grasping section is substantially circular in shape, and the cross-sectional area of the grasping section gradually decreases along a path of travel from the base portion to the tip portion to form a generally conical shape, wherein the grasping section further comprising a loop connected to the tip portion.

9. The plug of claim 8, wherein the loop projects longitudinally from the tip portion in the direction opposite the insertion section.

10. The plug of claim 7, further comprising a tab connected to the tip portion.

11. The plug of claim 10, wherein the tab projects longitudinally from the tip portion in the direction opposite the insertion section.

12. The plug of claim 7, wherein the retaining section is generally cylindrical in shape.

13. A plug for the end of a drain tube, the drain tube being for introduction into a patient during a medical procedure through an opening in the patient's body leading into the interior of the patient's body, wherein a medical instrument is used to extract the drain tube out through the opening in the patient's body, the plug comprising:

(a) an elongated insertion section of a predetermined cross-sectional area for slidable insertion into one end of the drain tube;

(b) a grasping section for gasping by the medical instrument, the grasping section projecting longitudinally from the insertion section, the grasping section including a tip portion opposite the insertion section and a base portion located between the tip portion and the insertion section, the base portion having a cross-sectional area larger than the cross-sectional area of the insertion section, wherein the cross-sectional area of the grasping section decreases in the direction extending away from the insertion section, wherein the base portion of the grasping section is substantially circular in shape, and the cross-sectional area of the grasping section gradually decreases along a path of travel from the base portion to the tip portion to form a generally conical shape;

(c) a generally cylindrical retaining section connects the grasping section to the insertion section, the retaining section having a diameter less than the diameter of the cylindrical portion; and, (d) (d) wherein the insertion section is substantially cylindrical, the diameter of the insertion section being greater than the diameter of the retaining section.

14. A plug for an elongated, flexible drain tube, the drain tube being for draining a surgical site within a patient, wherein one end of the drain tube is located at the surgical site, the drain tube extends through an incision in the patient to the exterior of the patient wherein a medical instrument is used to extend the drain tube through the incision, the plug comprising:

(a) an insertion section having a longitudinal central axis, a width, and a predetermined cross-sectional area for slidable insertion into one end of the drain tube;

(b) thin-section projection means having a width and projecting from the insertion section for presenting a thin cross-section relative to the width of the insertion section for grasping by the medical instrument;

(c) a guiding section disposed between the insertion section and the thin-section projection means, the guiding section having a width larger than the width of the insertion section; and (d) a retaining section disposed between the guiding section and the insertion section, the retaining section having a maximum width smaller than the width of the guiding section.

15. The plug of claim 14, wherein the thin cross section of the projection means is substantially thinner than the width across the insertion section.

16. The plug of claim 14, wherein the thin-section projection means comprises a tab projecting longitudinally from the insertion section, the tab having a thickness substantially less than the width across the insertion section.

17. The plug of claim 16, wherein the tab includes a generally planar area and a rim extending around the margin of the tab of a thickness greater than the planar area.

18. The plug of claim 14, wherein the insertion section includes a first, rounded end, and a second end opposite the first end and connected to the retaining section.

19. The plug of claim 14, wherein the cross-sectional width of the insertion section is greater than the cross-sectional width of the retaining section.

20. The plug of claim 14, wherein the thin-section projection means comprises a loop.

21. The plug of claim 20 wherein the loop projects longitudinally from the insertion section.

* * * * *

UNITED STATES PATENT AND TRADEMARK OFFICE
CERTIFICATE OF CORRECTION

PATENT NO. : 5,697,911
DATED : December 16, 1997
INVENTOR(S) : R.J. Yarger

It is certified that error appears in the above-identified patent and that said Letters Patent is hereby corrected as shown below:

| COLUMN | LINE | |
|---|---|---|
| 9 (Claim 13, | 6 line 10) | "gasping" should read --grasping-- |
| 9 (Claim 13, | 25 line 29) | Delete "(d)" (second occurrence) |

Signed and Sealed this

Sixteenth Day of June, 1998

Attest:

BRUCE LEHMAN

Attesting Officer     Commissioner of Patents and Trademarks